(12) United States Patent
Morris et al.

(10) Patent No.: US 8,545,864 B2
(45) Date of Patent: Oct. 1, 2013

(54) HEMOSTATIC BONE GRAFT

(75) Inventors: John W. Morris, Beachwood, NJ (US);
David A. Knaack, Summit, NJ (US);
Lawrence A. Shimp, Morganville, NJ (US); Keyvan Behnam, Red Bank, NJ (US); Robert P. Skinner, Jackson, NJ (US); Randal R. Betz, Ocean City, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 674 days.

(21) Appl. No.: 11/773,775

(22) Filed: Jul. 5, 2007

(65) Prior Publication Data
US 2008/0063671 A1 Mar. 13, 2008

Related U.S. Application Data

(63) Continuation of application No. 11/556,072, filed on Nov. 2, 2006, now abandoned.

(60) Provisional application No. 60/732,978, filed on Nov. 2, 2005.

(51) Int. Cl.
*A61K 35/32* (2006.01)
*A61K 9/00* (2006.01)

(52) U.S. Cl.
USPC .......................... 424/422; 424/400; 424/549

(58) Field of Classification Search
None
See application file for complete search history.

(56) References Cited

U.S. PATENT DOCUMENTS

| | | | |
|---|---|---|---|
| 159,334 | A | 2/1875 | Kumpf |
| 781,882 | A | 2/1905 | Hunter |
| 2,516,438 | A | 7/1950 | Wheeler |
| 2,968,593 | A | 1/1961 | Rapkin |
| 3,458,397 | A | 7/1969 | Myers et al. |
| 3,609,867 | A | 10/1971 | Hodosh |
| 3,739,773 | A | 6/1973 | Schmitt et al. |
| 3,790,507 | A | 2/1974 | Hodosh |
| 3,829,904 | A | 8/1974 | Ling et al. |

(Continued)

FOREIGN PATENT DOCUMENTS

| | | |
|---|---|---|
| DE | 179 833 | 2/1905 |
| DE | 44 34 459 | 4/1996 |

(Continued)

OTHER PUBLICATIONS

Robert A. Stairs. Calculation of surface tension of salt solutions: effective polarizability of solvated Ions. Can. J. Chem. 73: 781-787. 1995 found on website http://article.pubs.nrc-cnrc.gc.ca/ppv/RPViewDoc?issn=1480-3291&volume=73&issue=6&startPage=781.*

(Continued)

*Primary Examiner* — Scott Long
*Assistant Examiner* — Sarah Alawadi
(74) *Attorney, Agent, or Firm* — Sorell Lenna & Schmidt LLP

(57) ABSTRACT

The present invention provides a hemostatic bone graft product and method. Hemostatic bone grafts may include demineralized bone matrix in combination with additives. In one embodiment, the graft comprises demineralized bone and polyethylene glycol. Methods for producing the hemostatic bone graft may include mixing demineralized bone with additives to facilitate protein precipitation, surface tension reduction in blood, and/or a cytolytic effect on cells at a bleeding site.

16 Claims, 3 Drawing Sheets

(56) References Cited

U.S. PATENT DOCUMENTS

| | | | |
|---|---|---|---|
| 3,891,997 A | 7/1975 | Herbert | |
| 3,922,726 A | 12/1975 | Trentani et al. | |
| 3,947,287 A * | 3/1976 | Belde et al. | 106/413 |
| 4,059,684 A | 11/1977 | Gross et al. | |
| 4,123,806 A | 11/1978 | Amstutz et al. | |
| 4,134,792 A * | 1/1979 | Boguslaski et al. | 435/4 |
| 4,172,128 A | 10/1979 | Thiele et al. | |
| 4,191,747 A | 3/1980 | Scheicher | |
| 4,209,434 A | 6/1980 | Wilson et al. | |
| 4,224,698 A | 9/1980 | Hopson | |
| 4,291,013 A | 9/1981 | Wahlig et al. | |
| 4,294,753 A | 10/1981 | Urist | |
| 4,355,331 A | 10/1982 | Georges et al. | |
| 4,363,319 A * | 12/1982 | Altshuler | 604/304 |
| 4,394,370 A | 7/1983 | Jefferies | |
| 4,430,760 A | 2/1984 | Smestad | |
| 4,440,370 A | 4/1984 | Rood | |
| 4,440,750 A | 4/1984 | Glowacki et al. | |
| 4,450,592 A | 5/1984 | Niederer et al. | |
| 4,458,733 A | 7/1984 | Lyons | |
| 4,472,840 A | 9/1984 | Jefferies | |
| 4,485,097 A | 11/1984 | Bell | |
| 4,512,038 A | 4/1985 | Alexander et al. | |
| 4,516,276 A | 5/1985 | Mittelmeier et al. | |
| 4,563,350 A | 1/1986 | Nathan et al. | |
| 4,563,489 A | 1/1986 | Urist | |
| 4,581,030 A | 4/1986 | Bruns et al. | |
| 4,595,713 A | 6/1986 | St. John | |
| 4,620,327 A | 11/1986 | Caplan et al. | |
| 4,623,553 A | 11/1986 | Ries et al. | |
| 4,627,853 A | 12/1986 | Campbell et al. | |
| 4,627,931 A | 12/1986 | Malik | |
| 4,636,526 A | 1/1987 | Dorman et al. | |
| 4,678,470 A | 7/1987 | Nashef et al. | |
| 4,698,375 A | 10/1987 | Dorman et al. | |
| 4,709,703 A | 12/1987 | Lazarow et al. | |
| 4,743,259 A | 5/1988 | Bolander et al. | |
| 4,795,463 A | 1/1989 | Gerow | |
| 4,795,467 A | 1/1989 | Piez et al. | |
| 4,822,349 A * | 4/1989 | Hursey et al. | 424/445 |
| 4,824,939 A | 4/1989 | Simpson | |
| 4,842,604 A | 6/1989 | Dorman et al. | |
| 4,857,269 A | 8/1989 | Wang et al. | |
| 4,863,472 A | 9/1989 | Tormala et al. | |
| 4,888,366 A | 12/1989 | Chu et al. | |
| 4,902,296 A | 2/1990 | Bolander et al. | |
| 4,919,939 A | 4/1990 | Baker | |
| 4,932,973 A | 6/1990 | Gendler | |
| 4,946,792 A | 8/1990 | O'Leary | |
| 4,950,296 A | 8/1990 | McIntyre | |
| 4,961,707 A | 10/1990 | Magnusson et al. | |
| 4,975,526 A | 12/1990 | Kuberasampath et al. | |
| 4,994,030 A | 2/1991 | Glowczewskie, Jr. et al. | |
| 5,001,169 A | 3/1991 | Nathan et al. | |
| 5,007,930 A | 4/1991 | Dorman et al. | |
| 5,015,247 A | 5/1991 | Michelson | |
| 5,032,445 A | 7/1991 | Scantlebury et al. | |
| 5,053,049 A | 10/1991 | Campbell | |
| 5,073,373 A | 12/1991 | O'Leary et al. | |
| 5,092,887 A | 3/1992 | Gendler | |
| 5,108,399 A | 4/1992 | Eitenmuller et al. | |
| 5,112,354 A | 5/1992 | Sires | |
| 5,123,925 A | 6/1992 | Smestad et al. | |
| 5,139,527 A | 8/1992 | Redl et al. | |
| 5,162,114 A | 11/1992 | Kuberasampath et al. | |
| 5,171,278 A | 12/1992 | Pisharodi | |
| 5,171,574 A | 12/1992 | Kuberasampath et al. | |
| 5,197,882 A | 3/1993 | Jernberg | |
| 5,207,710 A | 5/1993 | Chu et al. | |
| 5,236,456 A | 8/1993 | O'Leary et al. | |
| 5,284,655 A | 2/1994 | Bogdansky et al. | |
| 5,290,558 A * | 3/1994 | O'Leary et al. | 424/422 |
| 5,298,254 A | 3/1994 | Prewett et al. | |
| 5,306,304 A | 4/1994 | Gendler | |
| 5,314,476 A | 5/1994 | Prewett et al. | |
| 5,314,478 A | 5/1994 | Oka et al. | |
| 5,329,846 A | 7/1994 | Bonutti | |
| 5,343,877 A | 9/1994 | Park | |
| 5,366,507 A | 11/1994 | Sottosanti | |
| 5,368,859 A | 11/1994 | Dunn et al. | |
| 5,405,390 A | 4/1995 | O'Leary et al. | |
| 5,405,402 A | 4/1995 | Dye et al. | |
| 5,425,639 A | 6/1995 | Anders | |
| 5,425,762 A | 6/1995 | Muller | |
| 5,432,000 A * | 7/1995 | Young et al. | 428/372 |
| 5,439,684 A | 8/1995 | Prewett et al. | |
| 5,441,517 A | 8/1995 | Kensey et al. | |
| 5,447,725 A | 9/1995 | Damani et al. | |
| 5,449,375 A | 9/1995 | Vidal et al. | |
| 5,455,041 A | 10/1995 | Genco et al. | |
| 5,464,439 A | 11/1995 | Gendler | |
| 5,476,880 A | 12/1995 | Cooke et al. | |
| 5,480,436 A | 1/1996 | Bakker et al. | |
| 5,484,601 A | 1/1996 | O'Leary et al. | |
| 5,490,962 A | 2/1996 | Cima et al. | |
| 5,496,375 A | 3/1996 | Sisk et al. | |
| 5,507,813 A * | 4/1996 | Dowd et al. | 623/23.63 |
| 5,510,396 A | 4/1996 | Prewett et al. | |
| 5,518,680 A | 5/1996 | Cima et al. | |
| 5,531,791 A | 7/1996 | Wolfinbarger, Jr. | |
| 5,545,222 A | 8/1996 | Bonutti | |
| 5,556,430 A | 9/1996 | Gendler | |
| 5,567,806 A | 10/1996 | Abdul-Malak et al. | |
| 5,607,269 A | 3/1997 | Dowd et al. | |
| 5,641,518 A | 6/1997 | Badylak et al. | |
| 5,656,593 A | 8/1997 | Kuberasampath et al. | |
| 5,662,710 A | 9/1997 | Bonutti | |
| 5,676,146 A | 10/1997 | Scarborough | |
| 5,683,459 A | 11/1997 | Brekke | |
| 5,700,479 A | 12/1997 | Lundgren | |
| 5,707,962 A | 1/1998 | Chen et al. | |
| 5,723,117 A * | 3/1998 | Nakai et al. | 424/85.2 |
| 5,727,945 A | 3/1998 | Dannenbaum | |
| 5,782,919 A | 7/1998 | Zdeblick et al. | |
| 5,807,437 A | 9/1998 | Sachs et al. | |
| 5,846,484 A | 12/1998 | Scarborough et al. | |
| 5,888,219 A | 3/1999 | Bonutti | |
| 5,899,939 A | 5/1999 | Boyce et al. | |
| 5,910,315 A | 6/1999 | Stevenson et al. | |
| 5,922,753 A | 7/1999 | Petrie et al. | |
| 6,030,635 A | 2/2000 | Gertzman et al. | |
| 6,090,998 A | 7/2000 | Grooms et al. | |
| 6,123,731 A | 9/2000 | Boyce et al. | |
| 6,132,472 A | 10/2000 | Bonutti | |
| 6,206,923 B1 | 3/2001 | Boyd et al. | |
| 6,224,630 B1 | 5/2001 | Bao et al. | |
| 6,294,187 B1 | 9/2001 | Boyce et al. | |
| 6,311,690 B1 | 11/2001 | Jefferies | |
| 6,326,018 B1 | 12/2001 | Gertzman et al. | |
| 6,340,477 B1 | 1/2002 | Anderson | |
| 6,361,565 B1 | 3/2002 | Bonutti | |
| 6,375,663 B1 | 4/2002 | Ebner et al. | |
| 6,432,436 B1 | 8/2002 | Gertzman et al. | |
| 6,436,138 B1 | 8/2002 | Dowd et al. | |
| 6,436,139 B1 | 8/2002 | Shapiro et al. | |
| 6,437,018 B1 | 8/2002 | Gertzman et al. | |
| 6,458,375 B1 | 10/2002 | Gertzman et al. | |
| 6,565,884 B2 * | 5/2003 | Nimni | 424/484 |
| 6,599,515 B1 | 7/2003 | Delmotte | |
| 6,599,520 B2 | 7/2003 | Scarborough et al. | |
| 6,616,698 B2 | 9/2003 | Scarborough | |
| 6,630,153 B2 | 10/2003 | Long et al. | |
| 6,632,247 B2 | 10/2003 | Boyer, II et al. | |
| 6,638,309 B2 | 10/2003 | Bonutti | |
| 6,652,592 B1 | 11/2003 | Grooms et al. | |
| 6,652,593 B2 | 11/2003 | Boyer, II et al. | |
| 6,706,067 B2 | 3/2004 | Shimp et al. | |
| RE38,522 E | 5/2004 | Gertzman et al. | |
| 6,733,534 B2 | 5/2004 | Sherman | |
| 6,736,853 B2 | 5/2004 | Bonutti | |
| 6,776,938 B2 | 8/2004 | Bonutti | |
| 6,808,585 B2 | 10/2004 | Boyce et al. | |
| 6,843,807 B1 | 1/2005 | Boyce et al. | |
| 6,855,169 B2 | 2/2005 | Boyer, II et al. | |

| | | | |
|---|---|---|---|
| 6,863,694 B1 | 3/2005 | Boyce et al. | |
| 6,911,212 B2 | 6/2005 | Gertzman et al. | |
| 6,913,621 B2 | 7/2005 | Boyd et al. | |
| 7,045,141 B2 | 5/2006 | Merboth et al. | |
| 7,163,691 B2 | 1/2007 | Knaack et al. | |
| RE39,587 E | 4/2007 | Gertzman et al. | |
| 7,311,713 B2 | 12/2007 | Johnson et al. | |
| 7,323,193 B2 | 1/2008 | Morris et al. | |
| 2001/0020186 A1 | 9/2001 | Boyce et al. | |
| 2002/0026244 A1* | 2/2002 | Trieu | 623/17.16 |
| 2002/0029084 A1 | 3/2002 | Paul et al. | |
| 2002/0035401 A1 | 3/2002 | Boyce et al. | |
| 2002/0055143 A1* | 5/2002 | Bell et al. | 435/69.1 |
| 2002/0107570 A1 | 8/2002 | Sybert et al. | |
| 2002/0120338 A1 | 8/2002 | Boyer, II et al. | |
| 2002/0161449 A1 | 10/2002 | Muschler | |
| 2003/0009235 A1 | 1/2003 | Manrique et al. | |
| 2003/0036800 A1 | 2/2003 | Meredith | |
| 2003/0045934 A1 | 3/2003 | Bonutti | |
| 2003/0093154 A1 | 5/2003 | Estes et al. | |
| 2004/0023387 A1 | 2/2004 | Morris et al. | |
| 2004/0062790 A1* | 4/2004 | Constantine et al. | 424/426 |
| 2004/0097612 A1 | 5/2004 | Rosenberg et al. | |
| 2004/0220681 A1* | 11/2004 | Cole et al. | 623/23.62 |
| 2005/0065214 A1* | 3/2005 | Kronenthal | 514/557 |
| 2005/0170396 A1* | 8/2005 | Baker et al. | 435/6 |
| 2006/0002976 A1 | 1/2006 | Kronenthal | |
| 2006/0013857 A1 | 1/2006 | Kronenthal | |
| 2006/0030948 A1 | 2/2006 | Manrique et al. | |
| 2006/0147545 A1 | 7/2006 | Scarborough et al. | |
| 2006/0280801 A1 | 12/2006 | Kronenthal | |

FOREIGN PATENT DOCUMENTS

| | | |
|---|---|---|
| DE | 29608321 | 8/1996 |
| EP | 0 082 621 | 6/1983 |
| EP | 0 243 151 | 10/1987 |
| EP | 0 267 015 | 5/1988 |
| EP | 0 321 442 A3 | 6/1989 |
| EP | 0 366 029 A3 | 5/1990 |
| EP | 0 406 856 | 1/1991 |
| EP | 0405429 | 1/1991 |
| EP | 0 411 925 | 2/1991 |
| EP | 0 413 492 | 2/1991 |
| EP | 0 419 275 | 3/1991 |
| EP | 0 483 944 | 5/1992 |
| EP | 0 495 284 | 7/1992 |
| EP | 0 520 237 | 12/1992 |
| EP | 0 555 807 | 8/1993 |
| EP | 0 567 391 | 10/1993 |
| EP | 0 693 523 | 1/1996 |
| EP | 1 142 581 A2 | 10/2001 |
| FR | 2691901 | 12/1993 |
| GB | 2175807 | 10/1986 |
| JP | 9059/1986 | 3/1986 |
| JP | 2121652 | 5/1990 |
| JP | 3210270 A | 9/1991 |
| JP | 4097747 A | 2/1992 |
| JP | 9506281 | 6/1997 |
| RU | 0880425 | 11/1981 |
| WO | WO 86/07265 | 12/1986 |
| WO | WO 89/04646 | 6/1989 |
| WO | WO 89/11880 | 12/1989 |
| WO | WO 94/21196 | 9/1994 |
| WO | WO 95/15776 | 6/1995 |
| WO | WO 96/39203 | 12/1996 |
| WO | WO 97/25941 | 7/1997 |
| WO | WO 98/00183 | 1/1998 |
| WO | WO 98/17209 | 4/1998 |
| WO | WO 98/40113 | 9/1998 |
| WO | WO 99/39757 A1 | 8/1999 |
| WO | WO 01/08584 * | 5/2000 |
| WO | WO 00/34556 | 6/2000 |
| WO | WO 00/35510 | 6/2000 |
| WO | WO 00/50102 | 8/2000 |
| WO | WO/01/08584 * | 8/2001 |
| WO | WO 02/02156 | 1/2002 |
| WO | WO 02/47587 A | 6/2002 |
| WO | WO 2004/108023 A | 12/2004 |
| WO | WO2005/065396 * | 7/2005 |
| WO | WO 2006/057011 A2 | 6/2006 |
| WO | WO 2006/076712 A2 | 7/2006 |

OTHER PUBLICATIONS

E. Abel. The Vapor Phase above the System Sulfuric Acid-Water. J. Phys. Chem. 50(3) pp. 260-283. 1946. found on website http://pubs.acs.org/doi/abs/10.1021/j150447a011.*

JADA, vol. 133, Dec. 2002. http://jada.ada.org/cgi/reprint/133/12/1610-a.*

Abjornson et al., "A Novel Approach to Bone Grafting Substitutes", Society for Biomaterials, p. 1372 (2000).

Block, Michael S., D.M.D. et al., "Bone Maintenance 5 to 10 years After Sinus Grafting", J. Oral Maxillofacial Surg., vol. 56, pp. 706-714, 1998.

Bobyn et al., "The Optimum Pore Size for the Fixation of Porous-Surfaced Metal Implants by Ingrowth of Bone", Clinical Orthopaedics and Related Research, 1980, pp. 263-270.

Bolander et al.,"The Use of Demineralized Bone Matrix ion te Repair of Segmental Defects", *The Journal of Bone and Joint Surgery*, vol. 68-A, No. 8, pp. 1264-1273.

Bostrom et al., "Use of Bone Morphogeneic Protein-2 in the Rabbit Ulnar Nonunion Model", Clinical Orthopaedics and Related Research, No. 327, pp. 272-282 (1996).

Covey et al., "Clinical Induction of Bone Repair with Demineralized Bone Matrix or a Bone Morphogenetic Protein", Orthopaedic Review, Aug. 1989, vol. XVIII, No. 8, pp. 857-863.

Crowe et al., "Inhibition of Enzymatic Digestion of Amylose by Free Fatty Acids in Vitro Contributes to Resistant Starch Formation", J. Nutr. 130(8): 2006-2008, 2000.

Edwards et al., "Osteoinduction of Human Demineralized Bone: Characterization in a Rat Model", *Clinical Orthopaedics & Rel. Res.* 357:219-228, Dec. 1998.

Gekko et al., "Mechanism of Protein Stabilization by Glycerol: Preferential Hydration in Glycerol-Water Mixtures", vol. 20, No. 16, pp. 4667-5676 (1981).

Gepstein et al., "Bridging Large Defects in Bone by Demineralized Bone Matrix in the Form of a Powder", *The Journal of Bone and Joint Surgery*, vol. 69-A, No. 7, pp. 984-991, 1987.

Gher, Marlin E., et al., "Bone Grafting and Guided Bone Regeneration for Immediate Dental Implants in Humans", J. Periodontology, 1994, 65:881-891.

Glowacki et al., "Application of Biological Principle of Induced Osteogenesis for Craniofacial Defects", The Lancet, 1981, vol. 1, No. 8227, pp. 959-962.

Glowacki et al., "Demineralized Bone Implants", *Symposium on Horizons in Plastic Surgery*, vol. 12, No. 2, pp. 233-241, 1985.

Glowacki et al., "Fate of Mineralized and Demineralized Osseous Implants in Cranial Defects", Calcified Tissue Int. 33: 71-76, 1981.

Groeneveld et al., "Mineralized Processes in Demineralized Bone Matrix Grafts in Human Maxillary Sinus Floor Elevations", John Wiley & Sons, Inc. pp. 393-402 (1999).

Habal et al., "Autologous Corticocancellous Bone Paste for Long Bone Discontinuity Defects: An Experimental Approach", Annals of Plastic Surgery, Aug. 1985, vol. 15, No. 23, pp. 138-142.

Ito, Takayasu et al., "Sensitivity of Osteoinductive Activity of Demineralized and Defatted Rat Femur to Temperature and Furation of Heating", Clinical Orthopaedics and Related Research, No. 316, 1995, pp. 267-275.

Jurgensen, K., M.D. et al., "A New Biological Glue for Cartilage-Cartilage-Cartilage Interfaces: Tissue Transglutaminase", Journal of Bone and Joint Surgery, Inc., Feb. 1997, pp. 185-193.

Kaban et al., "treatment of Jaw Defects with Demineralized Bone Implants", Journal of Oral and Maxillofacial Surgery, pp. 623-626 (Jun. 6, 1998).

Kakiuchi et al., "Human Bone Matrix Gelatin as a Clinical Alloimplant", International Orthopaedics, 9, pp. 181-188 (1985).

Kiviranta et al., "The Rate fo Calcium Extraction During EDTA Decalcification from Thin Bone Slices as Assessed with Atomic Absorption Spectrophotometry", Histochemistry 68, 1980, pp. 119-127.

Kubler, et al., "Allogenic bone and Cartilage Morphogenesis", J. Craniomaxillofac. Surg. 19(7): 238-288, 1991.
Lewandrowski et al., "Flexural Rigidity in Partially Demineralized Diaphysical Bone Grafts," Clin. Ortho. Rel. Res. 317: 254-262, 1995.
Lewandrowski et al., "Kinetics of Cortical Bone Demineralization: controlled demineralization—a new method for modifying cortical bone allografts," J. Biomed. Mater. Res. 31:365-372, 1996.
McLaughlin et al., "Enhancements of Bone Ingrowth by the Use of Bone Matrix as a Biologic Cement", Clinical Orthopaedics and Related Research, No. 183, pp. 255-261 (Mar. 1984).
Meijer et al., Radiographic Evaluation of Mandibular Augmentation with Prefabricated Hydroxylapatite/Fibrin Glue Imlants, Journal of Oral and Maxillofacial Surgery, 1997, pp. 138-145.
Mellonig, "Decalicified Freeze-Dried Bone Allograft as an Implant Material in Human Periodontal Defects", *The International Journal of Periodontics and Restorative Dentistry*, pp. 41-45, 1984.
Mellonig, James T. D.D.S., M.S., "Bone Allografts in Periodontal Therapy", Clinical Orthopaedics and Related Research, No. 324, Mar. 1996.
Mulliken, J.B. and Glowacki, "Induced Osteogenesis for Repair and Construction in the Craniofacial Region", J. Plastic and Reconstructive Surgery, May 1980, p. 553-559.
Neigal et al., "Use of Demineralized Bone Implants in Orbital and Craniofacial", Opthal. Plast. Reconstrs. Surg., 12: 108-120, 1996.
Paralkar, et al., PNAS, 100(11): 6736-6740, 2003.
Parma-Benfenati, S., et al., "Histologic Evaluation of New Attachment Utilizing a Titanium-Reinforced Barrier Membrane in a Nucogingival Recession Defect. A Case Report", J. Periodontology, Jul. 1998.
Perez, B.J. et al., "Mechanical properties of a discontinous random fiber composite for totally bioabsorbable fracture fixation devices", Paper presented in : Bioengineering Conference, 1995, Proceedings of the 1995 IEEE 21st Annual Northeast, May 22-23, 1995, pp. 55-56.
Product literature for Bio-Gide®, Resorbable barrier membrane from OsteoHealth Co., Division of Luitpold Pharmaceutical, Inc. 1998.
Product literature for Gore Resolut XT, Bioabsorbable membrane from Gore Regenerative Technologies, Palm Beach Gardens, FL 1998.
Ray, Robert et al. "Bone Implants: Preliminary Report of an Experimental Study", Journal of Bone and Joint Surgery, vol. 29A (5), Oct. 1957.
Reddi et al., *Proc. Natl. Acad. Sci.* 69:1601-1605, 1972.
Russell et al., *Orthopaedics*, 22(5):524-53, May 1, 1999.
Stevenson et al., "Factors Affecting Bone Graft Incorporation", Clinical Orthopaedics and Related Research, No. 323, 1996, pp. 66-74.
The Term "Substantially", Merriam-Webster Online Dictionary, at the web—http://www.m-w.com, p. 1.
Teparat, Thitiwan et al., "Clinical Comparison of Bioabsorbable Barriers With Non-Resorbable Barriers in Guided Tissue Regeneration in the Treatment of Human Intrabony Defects", J. Periodontology, Jun. 1998.
Todescan et al., "A Small Animal Model for Investigating Endosseous Dental Impants:Effect of Graft Materials on Healing of Endoss, Porous-Surfaced Implants Placed in a Fresh Extraction Socket", *The Journal of Oral and Maxillofacial Implants*, vol. 2, No. 2, pp. 217-223, 1987.
Ueland et al., "Increased Cortical Bone Content of Insulin-Like Growth Factors in Acromegalic Patients", J. Clin. Endocrinol. Metab., 84(1): 123-127, 1999.

Urist, M.R. et al., "The Bone Induction Principle", *Clin. Orthop. Rel. Res.* 53:243-283, 1967.
Urist, M.R., "Bone Formation by Autoinduction", *Science*, 150(698):893-9,1965.
Whiteman et al., *J. Hand. Surg.* 18B:487, 1993.
Whittaker et al., "Matrix Metalloproteinases and Their Inhibitors—Current Status and Future Challenges", Celltransmissions, 17(1): 3-14.
Xiaobo et al., *Orthop.*, No. 293, pp. 360-365, 1993.
Zhang, et al., "A Quantative Assessment of Osteoinductivity of Human Demineralized Bone Matrix", J. Periodontol. 68(11): 1076-1084, 1997.
Urist et al. "Bone Formation in Implants of Partially and Wholly Demineralized Bone Matrix," Clinical Orthopaedics and Related Research, vol. 71, pp. 271-278 (1970).
Grafton™ Allogenic Bone Matrix (ABM), Advertising Brochure, Advanced Processing of Human Allograft Bone, Osteotech, Inc., 1992.
Frenkel et al. "Use of Demineralized Bone Matrix Gel to Enhance Spine Fusion", 19th Annual Meeting of the Society for Biomaterials, Apr. 28-May 2, 1993, Birmingham, AL, p. 162.
Stevenson et al. "Long Bone Defect Healing Induced by a New Formulation of Rat Demineralized Bone Matrix Gel," 40th Annual Meeting, Orthopedic Research Society, Feb. 21-24, 1994, New Orleans, LA, p. 205-35.
Pedrozo, Hugo A. et al. "Growth Plate Chondrocytes Store Latent Transforming Growth Factor (TGF)-β1 in Their Matrix Through Latent TGF-β1 Binding Protein-1," *Jour. of Cellular Physiology*, 177(2): 343-354 (1997).
Bautista, Catalino M. et al. "Isolation of a novel insulin-like growth factor (IGF) binding protein from human bone: A potential candidate for fixing IGF-II in human bone," *Biochem. and Biophys. Research Communications*, 176(2): 756-763 (Apr. 30, 1991).
Mohan, S. "Insulin-Like Growth Factor Binding Proteins in Bone Cell Regulation," Growth Regulation, 3(1): 67-70 (1993).
Japanese Office Action dated Mar. 18, 2009, from related, co-pending application JP 2003-533987.
Ruppert, Rainer et al. "Human bone morphogenetic protein 2 contains a heparin-binding site which modifies its biological activity," *Eur. J. Biochem*, 237(1): 295-302 (1996).
Kubler, N. R. et al. "EHBMP-2: The first BMP-variant with osteoinductive properties," *Mund Kiefer Gesichtschir*, 3(1): S134-S139 (1999).
Reddi, A. Hari. "Interplay between bone morphogenetic proteins and cognate binding proteins in bone and cartilage development: noggin, chordin and DAN," *Arthritis Research*, 3(1): 1-5 (2001).
Gazzerro, Elisabetta et al. "Bone Morphogenetic Proteins Induce the Expression of Noggin, Which Limits Their Activity in Cultured Rat Osteoblasts," *Jour. of Clin. Invest.*, 102(12): 2106-2114 (1998).
Yamaguchi, Akira. "Recent advances in researches on bone formation—Role of BMP in bone formation," Nihon Rinsyo, 56(6): 1406-1411 (1998).
Dallas, Sarah L. et al. "Dual Role for the Latent Transforming Growth Factor-β Binding Protein in Storage of Latent TGF-β in the Extracellular Matrix and as a Structural Matrix Protein," *Jour. of Cell Biol.*, 131(2): 539-549 (1995).
Pedrozo, Hugo A. et al. "Vitamin $D_3$ Metabolites Regulate LTBP1 and Latent TGF-β1 Expression and Latent TGF-β1 Incorporation in the Extracellular Matrix of Chohdrocytes," *Jour. of Cell. Biochem.*, 72(1): 151-165 (1999).

\* cited by examiner

HEMOSTATIC BONE GRAFT

CROSS-REFERENCE TO RELATED APPLICATION

This application claims priority to U.S. Provisional Application No. 60/732,978, filed on Nov. 2, 2005, the content of which is incorporated in its entirety by reference herein.

FIELD OF THE INVENTION

The present invention relates to hemostatic bone graft materials, and to a process for making the hemostatic bone graft materials. More specifically, the present invention relates to hemostatic bone grafts that, in addition to reducing or stopping bleeding in a surgical-type setting, may serve as an osteoinductive and/or an osteoconductive material.

BACKGROUND OF THE INVENTION

Hemostasis, or the stoppage of blood flow, results from plugging blood flow or from forming a blood clot. Plugging blood flow can be accomplished by exerting pressure on or by sealing the bleeding site. The formation of blood clots results from at least three pathways: (1) by a clot cascade; (2) by rapid constriction of the injured vessel; (3) and by the aggregation of platelets to form a plug on the injured surface of the blood vessel.

The clot cascade pathway is initiated by a series of transformations from inactive zymogens to active proteins. An activated protein, or clotting factor, catalyzes the activation of the next protein. Because the pathway is catalytic in nature, only very small amounts of protein need to be activated in order to activate the clotting process.

Clot cascades are calcium-dependent processes and are induced by either intrinsic or extrinsic means. In the case of induction by intrinsic means, clot formation components present in blood are triggered by contact with an abnormal surface, as compared to normal vascular tissue. In the case of clotting induction by extrinsic means, substances not normally present in blood are added. The clotting cascade can be initiated by denaturing clot proteins, which can be accomplished by the removal of water, including the rapid removal of water; by the addition of heat; or by chemical precipitation.

Clotting cascades, whether induced by intrinsic or extrinsic means, ultimately follow a common pathway. The common pathway includes activating clotting factor X, which then converts prothrombin to thrombin by its proteolytic action. In addition, activation of prothrombin is promoted by the presence of calcium ions and by phospholipid surfaces. Thrombin is responsible for cleaving fibrinogen into fibrin monomers, which results in the formation of a fibrin clot. Fibrinogen is an elongated protein consisting of six polypeptide chains. It is highly soluble in plasma. Upon cleavage of fibrinogen by the proteolytic action of thrombin, four peptide bonds are cleaved, and insoluble fibrin monomers result. Those fibrin monomers spontaneously associate to form fibrin, which takes the form of long, insoluble fibers. Fibrin monomers spontaneously associate to form a fibrin clot because of the removal of negatively charged groups found in fibrinogen. The release of the negatively charged groups by thrombin changes the surface-charge pattern of fibrin monomers, which in turn leads to their aggregation and to hemostasis.

Hemostatic agents control blood loss. Bee's wax is generally known to act as a hemostatic plug and has been used to control bone bleeding. Generally, bee's wax resists hydrostatic pressure and is cohesive. Bee's wax, however, is not resorbable and does not allow bone to grow in the site where it is placed. Therefore, bee's wax is undesirable for controlling blood loss from bleeding bone or in areas associated with bone.

In the field of internal medical care, such as internal surgery, there is a need for controlling bleeding in order to prevent excessive blood loss or hemorrhage. There also is a need to provide a product that can be easily applied to a bleeding site that also can promote both blood clotting and bone growth.

BRIEF SUMMARY OF THE INVENTION

A biocompatible hemostatic bone graft that aids in the reduction of operative and post-operative bleeding is provided. The hemostatic bone graft may be bioactive and may induce osteoconductive and/or osteoinductive activity upon implantation.

The hemostatic bone grafts of the present invention may cause blood clotting. The hemostatic bone grafts of the present invention may be waxy so as to plug a bleeding site. In one embodiment, a biocompatible material for promoting blood clotting may include demineralized bone matrix (DBM) and a clot producing material. According to another embodiment, DBM may be fibrous in order to cause blood clotting. Clot producing material, according to certain embodiments, may include polyethylene glycol (PEG), aluminum, hydroxyapatite, which may be unsintered, absorbents, absorbent DBM that has been treated to alter the surface tension of surrounding liquids to provide for rapid water uptake into the bone, a hydroscopic agent, a surface tension reducing material, and/or a substance capable of inducing protein precipitation, such as those materials capable of removing the water of solvation from protein. In another embodiment, biocompatible materials for blood clotting include bone, biocompatible polymers, or combinations thereof that are configured as wicking materials such as capillary tubes, small fibers, or U-shaped materials that allow blood to clot upon wicking.

In another embodiment, the hemostatic bone grafts of the present invention may contain both demineralized bone and a sealant. The sealant may take the form of a waxy, sticky substance, including lipids, PEG, lecithin, saccharides such as polysaccharides, fatty acids, including high molecular weight fatty acids, other suitable sealants, or combinations of these. Glycerol may be added to the waxy material in some embodiments.

In one embodiment, the invention comprises substantially water-free demineralized bone and lecithin. The bone may be in a concentration high enough to establish substantial contiguity of the bone, which may be done using bone fibers or bone particles. A surface tension reduction material also may be used. For example, PEG may be used, such as to coat the bone, to provide for increase uptake of water into the bone. This embodiment may be minimally moldable or generally stiff, and may be capable of being softened at body or elevated temperatures.

In the various embodiments of the invention, any suitable type of bone materials can be used, including substantially fully demineralized bone, partially demineralized bone, surface demineralized bone, or nondemineralized bone, or mineralized bone.

According to some embodiments, a surface tension reduction material may include glycerol, non-crystalline starch, amphipathic zwitterions, a polyalcohol, and/or aluminum sulfate, other suitable materials, or combinations of these. In some embodiments, ethanol may be used.

A protein precipitating agent used in accordance with some embodiments may include ammonium sulfate, PEG, a hydrogel, unsintered hydroxyapatite, calcium phosphate, other suitable agents, or combinations of these. Other embodiments may include as a clot producing material materials that absorb water from blood, leading to clot formation. In another embodiment, a biocompatible material for promoting blood clotting includes demineralized bone matrix and a hydrostatic agent, in which case the biocompatible material may take the form of a sheet, a powder, a matrix, a paste, a wax, a gel, or other suitable form. Demineralized bone matrix, according to some embodiments, may include fibrous demineralized bone. A hydrostatic agent used in accordance with particular embodiments may include the use of waxes, solid fatty acids or derivatives, non-crystalline starches, PEG, or combinations thereof.

Another embodiment provides a biocompatible material for promoting blood clotting that includes demineralized bone matrix, a protein precipitating agent, and a material that promotes water uptake by the demineralized bone. Because PEG affects both protein precipitation and promotes water uptake by DBM, according to certain embodiments, PEG may be used as either a protein precipitating agent or as a material that promotes water uptake by DBM.

According to another embodiment, a method for promoting blood clotting is provided that includes forming a biocompatible product having a mixture of demineralized bone matrix and a clot producing material, and placing the product on a bleeding site. The method may include adding lyophilized demineralized bone matrix and/or may include lyophilizing the mixture. The method may include adding fibrous demineralized bone matrix as the demineralized bone matrix, according to certain embodiments. The biocompatible material according to some embodiments may take the form of a sheet, a powder, a matrix, a wax, a paste, or a gel.

Another method for producing a biocompatible material for promoting blood clotting includes mixing lyophilized demineralized bone matrix and PEG. The demineralized bone matrix and PEG may be in a ratio of about 1:9, about 3:2, a ratio in between, or any other suitable ratio. The mix may further include about four parts water to a mixture of about three parts demineralized bone matrix to about two parts PEG. According to certain embodiments, the PEG may be melted in order to facilitate blending with the DBM. The mixture may be lyophilized and/or the demineralized bone matrix may be lyophilized, according to some embodiments.

Included in another method for producing a biocompatible material for promoting blood clotting is mixing demineralized bone matrix and aluminum sulfate, freezing the mixture, and lyophilizing the mixture. Yet another method for producing a biocompatible material for promoting blood clotting includes mixing demineralized bone matrix and lecithin. The mixture may be heated and/or smoothed. Furthermore, the demineralized bone matrix may be smoothed. In other certain embodiments, the mixture may further include a carrier and a preservative. In another embodiment, the method may include treating the demineralized bone matrix with an alcohol, dissolving the lecithin in alcohol, forming a mixture by pouring the demineralized bone matrix solution over a sieve, pouring the lecithin dissolved in alcohol over the sieve, and then lyophilizing the mixture.

DETAILED DESCRIPTION OF THE INVENTION

A hemostatic bone graft is provided herein. The hemostatic bone graft reduces or stops blood flow from a bleeding site, such as bleeding bone, by promoting denaturing of clot proteins and/or by absorbing liquid. Additionally, inventive bone waxes are provided that are sticky and may be used to plug a bleeding site, and in some embodiments, trigger a clot cascade and promote bone growth. Thus, according to various embodiments, the hemostatic bone graft may promote clotting, act as a plug, and/or promote bone growth, or combinations of these and other properties. Hemostatic bone grafts can be described as osteoimplants, the details of which are further described in U.S. Pat. No. 6,843,807, the contents of which are incorporated by reference herein.

In one embodiment, a reduced surface tension hemostatic lyophilized DBM is provided that scavenges and/or sequesters liquid from blood and other body fluids and/or assists in the clotting process to reduce post-operative bleeding. In some embodiments, the amount of DBM used in these absorptive formulations is such that particles are substantially contiguous, facilitating rapid water uptake throughout the preparation. For example, demineralized bone powder particles may be used in the absorptive formulations and is described in further detail in U.S. Pat. No. 5,073,373, the entire contents of which are incorporated herein by reference. The demineralized bone used in the present invention also can take the form of fibers, as disclosed in U.S. Pat. No. 5,507,813, which is incorporated by reference herein. The use of fibers may allow less bone to be used in the present invention, since particle contiguity can be assured with less bone than in particle forms.

The hemostatic bone grafts may comprise substantially water-free DBM in combination with other materials, and may be produced in a variety of forms, including powders, fibers, sheets, strips, blocks, matrices, putties, gels, and pastes. It should be understood that other calcium-based materials may be used as hemostats in addition to DBM or in combination with DBM, including calcium phosphate, unsintered hydroxyapatite, or calcined hydroxyapatite. This combination may be useful because addition of calcium can facilitate calcium-dependent processes, such as the clot cascade process.

Hemostatic bone grafts may also be formed of materials other than DBM, such as from biocompatible mineralized bone and/or polymers.

Figure 1:
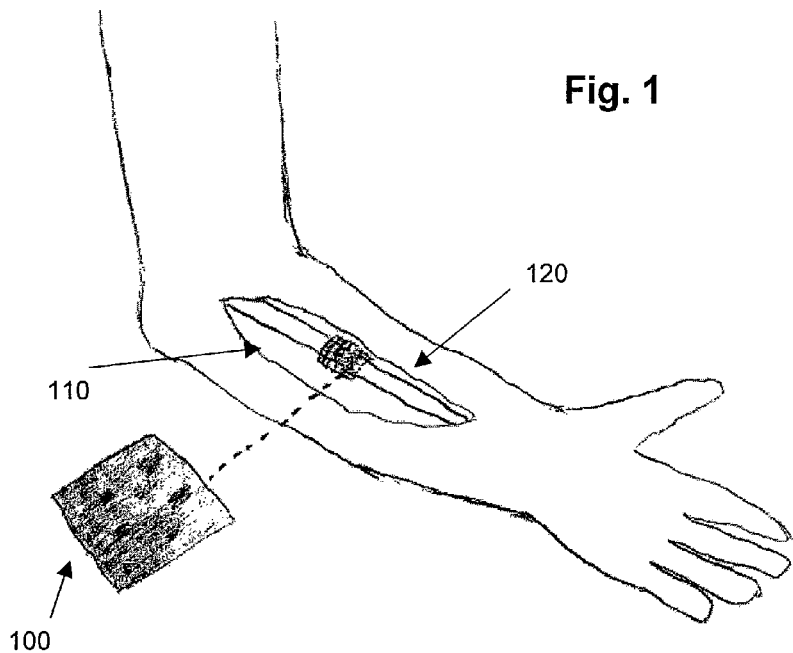
FIG. 1 depicts one embodiment of a material containing DBM for application to bone in a surgical setting.

FIG. 1 depicts one embodiment of a hemostatic bone graft that includes DBM-containing material for application to bone in a surgical setting. In FIG. 1, the DBM material is in the form of a sheet 100. Sheet 100 may be applied to a surgical site 110 on bone 120. Alternatively, the sheet 100 may be placed in areas in close proximity to bone. Sheet 100 may take the form of a woven material. The sheet may be pliable, allowing a surgeon to mold the DBM material around a bone.

Sheet 100 contains DBM that is a clot-producing product that absorbs liquid, triggering a clot cascade at a bleeding site where applied. In addition, the absorption characteristics of sheet 100 may be increased, such as by incorporating biocompatible materials that act as capillary tubes, or by other suitable techniques. For example, curled bone fibers (mineralized, nondemineralized, or demineralized) may be included in or on sheet 100. See U.S. Pat. No. 5,507,813. The bone fibers may be of any suitable geometry and surface characteristics to cause blood to be wicked up into the tubes. As a result, in addition to sheet 100 having increased wicking capabilities, the wicked blood may clot inside of the tubes.

Figure 2:
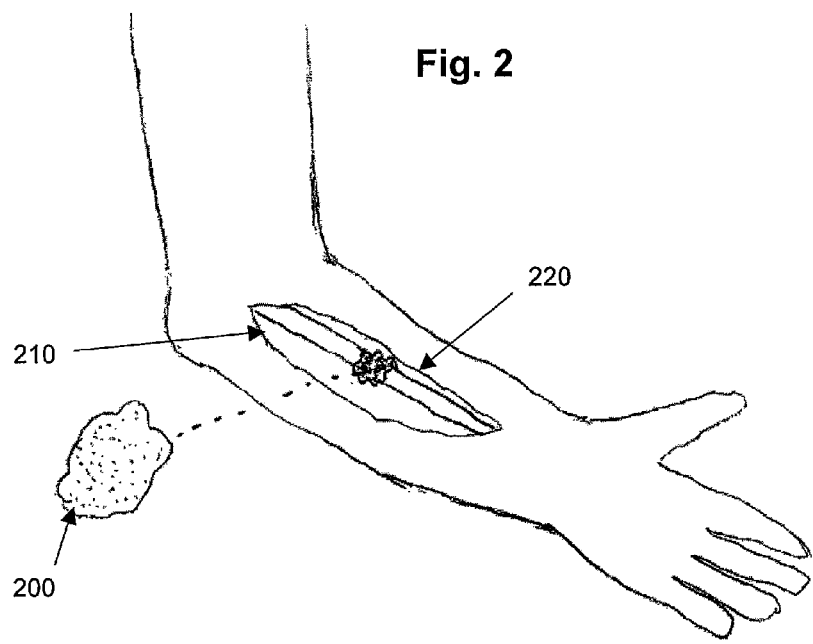
FIG. 2 depicts another embodiment of DBM-containing material for application to bone in a surgical setting.

FIG. 2 depicts another embodiment of a hemostatic bone graft that includes DBM-containing material for application to bone in a surgical setting. In FIG. 2, the DBM material is in the form of a putty 200. Putty 200 contains DBM. It first serves as a plug to stop blood flow, and then as a clot-producing material. The putty may have cohesive characteristics for sealing a bleeding site, in addition to possibly containing DBM. The composition may draw up liquids to trigger a clot cascade. In FIG. 2, putty 200 is applied to a surgical site 210 on bone 220. The putty 200 may be formed having any of a variety of desired consistencies, such as being malleable, waxy, sticky, and/or thick, etc., allowing a surgeon to mold the DBM material near or around bone. Using a DBM-based putty on or near bone may enable and promote bone growth.

Figure 3:
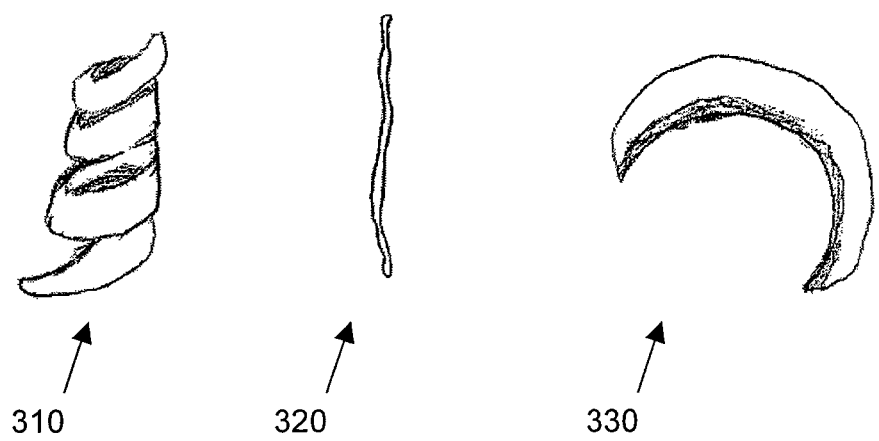
FIG. 3 depicts embodiments of materials for promoting blood clotting.

FIG. 3 depicts other embodiments of hemostatic bone graft materials that include biocompatible materials for wicking blood and allowing the wicked blood to clot. Curled fiber 310 is a biocompatible fiber such as mineralized, nondemineralized, or demineralized bone, polymers, other suitable materials, or combinations thereof that are shaped like tubes, including capillary tubes. These may promote blood wicking due to their geometry and surface characteristics. Curled fiber 310 may be produced from bone, for example, by milling cortical bone shafts with a milling bit, e.g., with an interrupted helical milling bit, that results in curled bone shavings resembling small capillary-like tubes. Curled fibrous bone may wick liquid and may be useful for wicking blood in bone grafting applications. Elongated fiber 320 is a biocompatible polymer fiber that may be used as a wicking tube or fiber. Any suitable material may be used. Examples of suitable materials include, but are not limited to, polymers (such as polyalkylenes (e.g., polyethylenes, polypropylenes, etc.), polyamides, polyesters, polyurethanes, poly(lactic acid-glycolic acid), poly(lactic acid), poly(glycolic acid), poly(glaxanone), poly(orthoesters), poly(pyrolicacid), poly(phosphazenes), etc.), cotton, silk, linen, metal, allograft tissue, autograft tissue, xenograft tissue, other suitable materials, or combinations of these. Suitable materials may be resorbable or non-resorbable polymer, or some of each. These materials may be used to form wicking materials, and may be synthetic, natural, etc. FIG. 3 also depicts U-shaped fibers 330 that may be formed of milled bone fibers that are not completely curled like curled fiber 310. U-shaped fiber 330 having a U-shaped cross-section may wick liquid from one end of the fiber to the other because the inner surface of the U-shaped fiber may enable wetting action to overcome the surface tension of the fluid, which allows blood to be transported across the length of the fiber. In some configurations, suitable dimensions for curled fibers, elongated fibers, and U-shaped fibers may be a diameter of 0.2 to 0.5 mm, and a length of 0.5 to 5 mm, or diameters and lengths. It is to be understood that "U-shaped" refers to any of a variety of shapes, where one end curls toward the other, and may include geometries that resemble in whole or in part a C, and S, or portions of these.

Although one of each of curled fiber 310, elongated fiber 320, and U-shaped fiber 330 is depicted in FIG. 3, it will be understood that a plurality of and combinations of any of the above-described fibers may be used as a blood clotting material. Furthermore, other suitable materials having a large surface area may be used in wicking blood in addition to those described above. Moreover, the above-described fibers may be incorporated into other materials such as DBM-containing materials including sheet 100 and putty 200.

According to certain embodiments that may incorporate DBM into the hemostatic bone graft, additives also may be combined with DBM to assist the clotting process. The additives may aid in water uptake, particularly by the DBM, for example by affecting the surface tension of water, and facilitating rapid uptake of water by the substantially water-free DBM. Additives combined with DBM in a mixture may also cause protein precipitation, may have a cytolytic effect on blood cells, or may serve to plug blood flow. The amount of DBM/additive-containing material required to have a hemostatic effect depends, in part, on the amount of DBM in the product. For products having from 25-40% DBM, the amount required may range from a 1:10 ratio of DBM to blood up to a 1:1 ratio of DBM to blood. Other suitable ratios, either greater or lesser, may be used for each of these. In addition, depending on the form of DBM, a greater or lesser amount by weight is required to trigger a hemostatic effect. For example, lower amounts of fibrous DBM are required to ensure contiguity of fibers and transfer of liquid to the interior of the preparation than with powdered DBM, and therefore wicks more liquid by weight compared to the powdered form. Factors that affect the amount of DBM/additive-containing material include the dryness of the mixture. As the dryness of the mixture increases, wicking capability increases.

According to certain embodiments, a hemostatic bone graft may be formed by treating DBM with PEG. PEG serves as a surface tension reducer and, when placed on bone, changes the surface tension in the surrounding area. PEG also is hemostatic and precipitates proteins. DBM coated with PEG rapidly absorbs moisture. Therefore, when used in a surgical setting, DBM/PEG products may serve as protein precipitating agents, moisture absorptives, and also osteoinductive materials. Various forms of PEG may be used as carriers for DBM matrices. For example, PEG is available in a variety of molecular weights, including 1,000, 1,500, and 10,000 molecular weight (MW) and other suitable molecular weights, each of which may be combined with DBM. Furthermore, blending various MW PEGs adjusts its handling characteristics. For example, the melting point and therefore consistency of blended PEG is different from the unblended form. Therefore, depending on the preparation method, the DBM/PEG product may have a variety of physical characteristics.

In various embodiments, all of the various constituents of the hemostatic bone graft, including the carrier and any added materials, are resorbed by the body, leaving the DBM behind. This allows the hemostatic bone graft to act as a hemostat during the period of time when bleeding is taking place, and as a bone growth-inducing material after the bleeding has been stopped. Thus, for example, when PEG is combined with DBM to prepare a hemostatic bone graft, the PEG will be resorbed by the patient's body, and the DBM will remain behind to induce bone growth at the defect site.

In one illustrative embodiment, PEG is used by combining 2.5 g DBM with 3.33 g sterile deionized water and 1.67 g 10,000 MW PEG. The materials are mixed, frozen for 1 hour, lyophilized for 24 hours, and stored. In other embodiments, 0.25 g DBM, 1.55-1.75 g PEG, and 3.33 g water are mixed, lyophilized, and stored. Alternatively, solvents may replace water, and rather than lyophilizing the mixture, solvents may be evaporated off from the mixture.

In another illustrative embodiment, 1.0 g DBM is combined with 3.0 g 1,000 MW PEG. The materials are mixed and stored.

In yet another illustrative embodiment, 3.0 g 1,500 MW PEG is heated until pliable and the pliable PEG is combined with 1.0 g DBM. The DBM/PEG combination is mixed and stored.

Figure 4:
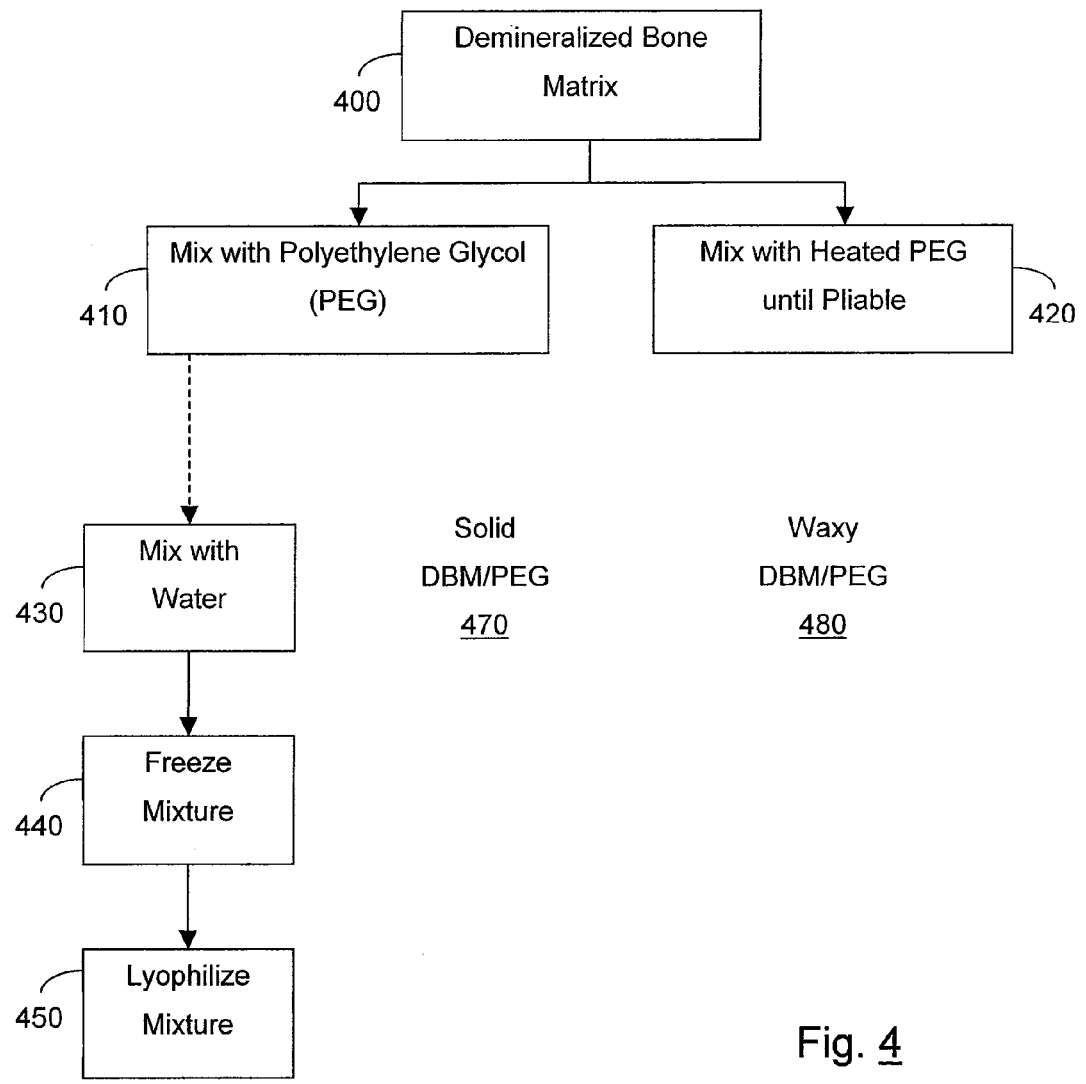
FIG. 4 depicts embodiments of products containing DBM and PEG.

Each of the above-described illustrative embodiments of combining PEG with DBM differs with respect to the handling properties of the finished product. FIG. 4 depicts the procedures for making each of the above-described embodiments and the physical properties of each of the resulting DBM/PEG products. According to FIG. 3, when DBM 400 is mixed with PEG 410 and water 430, is frozen 440, and lyophilized 450, a dry, powder-like DBM/PEG product 460 results. When DBM 400 is mixed with PEG 410, the resulting DBM/PEG product is solid 470. In another example, when DBM 400 is mixed with heated, pliable PEG 420, the resulting DBM/PEG product is waxy 480.

According to alternative embodiments of the present invention, hemostatic agents other than PEG, or in addition to PEG, may be combined with DBM. For example, mineralized bone material or DBM may be treated with aluminum sulfate. Aluminum sulfate acts as a hemostat by constricting blood vessels. Aluminum sulfate-coated DBM may also be used as an osteoinductive and osteoconductive material. In addition, aluminum sulfate-coated DBM, when air-dried, holds its form and is more rigid than untreated DBM. Therefore, aluminum sulfate-coated DBM may be a desirable osteoimplant for areas that require support and/or rigidity. Using aluminum sulfate in one embodiment includes treating all sides of a lyophilized, demineralized bone matrix with both 70% ethanol and a solution of deionized water and aluminum sulfate, where the aluminum sulfate originates from a 8.57 g styptic pencil (90% aluminum sulfate, 10% inert ingredients). The treated bone matrix may then be frozen and lyophilized for 48 hours, and the aluminum sulfate-coated DBM may be used as a hemostat in a surgical setting to retard or stop blood flow during surgery.

Additional hemostatic agents may be used in combination with DBM, according to further embodiments. For example, ethanol, ammonium sulfate, hydrogels, absorptive (unsintered) hydroxyapatite or calcium phosphate, and hygroscopic materials are precipitating agents that may be combined with DBM. Hydroxyapatite powder is able to absorb liquids and provides a large surface area that promotes blood clotting and bone growth. The combination of DBM and hydroxyapatite powder to form a hemostatic bone graft is advantageous over hydroxyapatite powder alone because the powder is difficult to place. Furthermore, the combination of DBM and hydroxyapatite may increase the product's ability to sequester liquid over DBM or hydroxyapatite alone.

Some embodiments include combining DBM with surface tension reducers. PEG is one type of surface tension reducer. According to certain embodiments, lecithin may be mixed with lyophilized, mineralized bone fiber to form a wax-like substance for use in filling voids and controlling blood loss during surgery. Lecithin is a waxy, thick, and sticky substance that may serve as a plug-like substance in a surgical-type setting.

One illustrative embodiment using lecithin comprises a 7.14 g mixture of lecithin-added bone fiber combined with 5.31 g starch and 3.58 g glycerol. The ingredients are ground to smooth for even hydration. The mixture is placed in an oven at 50° C. for 32 minutes and then placed in an oven at 80° C. for 2 minutes. The resulting mixture may be rolled into a ball and has the handling characteristics of wax. In alternative embodiments, the bone matrix may be DBM.

In another illustrative embodiment, a lecithin-added bone fiber mixture weighing 7.69 g is combined with 5.31 g carrier and 3.58 g preservative. Any clumps of fiber may be loosened and the carrier and preservative added. The mixture may be treated to smooth out any further clumps of tissue. The product is rolled into a ball and placed in ajar. The additional loosening step results in a looser yet solid mixture, without waxy characteristics.

In yet another illustrative embodiment, 31.25 g of bone fiber may be treated with a mixture of 469 ml HCl and 2 ml Triton, and then with 469 ml HCl and rinsed. Acid treatment of bone fiber demineralizes the fibers. According to certain embodiments, acid treatment may last between 30-50 minutes. After acid treatment, the demineralized bone fiber is treated with water, rinsed, and mixed with 235 ml ethanol. The mixture of ethanol and demineralized bone is mixed for several hours (i.e., 10-14 hours), poured through a sieve, and dried almost completely. To the resulting bone fiber product on the sieve is poured a solution of 31.25 g lecithin and 93.75 ml ethanol. Excess lecithin may be captured as the product is pressed of the excess. The resulting product weight can range from 52-67 g. The lecithin/demineralized bone matrix is lyophilized and a dry sheet of bone/lecithin results.

Lecithin is one type of surface tension reducer that may be used to control blood loss during surgery. In addition to lecithin, other materials may be mixed with DBM to reduce surface tension according to embodiments of the present invention, including fatty acids of any type, varieties of PEG, starch (including non-crystalline starch), carboxymethyl cellulose, maltodextrin, surfactants (such as fatty acids), ethanol, glycerol, salts, polyalcohols, amphipathic zwitterions, and wicking fibers described above in relation to FIG. 3 may be combined with DBM. Combinations of two or more of the above materials also may be used. A DBM and glycerol mixture provides a composition that can absorb liquid upon implantation, and the reduction of glycerol in the mixture increases the amount of liquid absorbed by DBM. Some existing bone graft products, including Osteotech's Grafton® DBM Gel, Grafton® DBM Putty, and Grafton® DBM Flex, include both DBM and glycerol. Glycerol may affect the surface tension of liquids in vivo. Glycerol-containing embodiments of the present hemostatic bone graft invention will contain less glycerol than used in the aforementioned Grafton® DBM products. Amphipathic zwitterions have hydrophilic and hydrophobic characteristics via positively charged cations and negatively charged anions in a neutral pH solution, and can be combined with DBM to reduce surface tension in liquids. It should be understood that combinations of the above-mentioned materials may be included with DBM to achieve the desired hemostatic result. For example, a combination of DBM, PEG, and lecithin may be used to form a hemostatic bone graft that precipitates proteins via PEG and that has cohesive properties via lecithin. In addition, fluidizing agents may be required to mix DBM and additives, and may include propylene glycol and glycerin.

Additives that have a cytolytic effect on cells may be mixed with DBM to form a hemostat. Cytolytic materials cause cells to burst, which may trigger clot cascades. In one embodiment, DBM is mixed with glycerol to form a hemostat. Embodiments may include mixing surfactants with DBM to form a hemostat. Other embodiments may include mixing cytolytic additives with DBM and surface tension reducers and/or protein precipitators.

The above-mentioned embodiments are not meant to be limiting. Rather, additional embodiments of the present invention are possible. For example, DBM may be combined with a sieve material, such as zeolite, see U.S. Pat. No. 4,822,349, which promotes adsorption of blood's water molecules into microscopic holes in the surfaces of its hollow particles.

Clotting factors and platelet molecules in blood are too large to enter the sieve material, and they remain concentrated in the surgical site, forming a strong, stable, natural clot that stays in place. Another example includes combining DBM and hyaluronic acid powder to form a dry hemostatic bone graft. In yet another embodiment, DBM may be combined with hygroscopic agents that affect fluid pressure or the exertion or transmission of pressure.

Various modifications may be made to the embodiments disclosed herein. For example, cancellous bone may be used in the hemostatic bone graft to promote rapid in-growth at a bleeding site and result in rapid fixation. In addition, hemostatic bone grafts material may be poured or placed into molds in order to shape the hemostatic bone graft material into useful shapes and sizes. The above description should not be construed as limiting, but merely as exemplifications of, preferred embodiments. Those skilled in the art will recognize other modifications within the scope and spirit of the present disclosure.

The invention claimed is:

1. A biocompatible material for promoting blood clotting comprising demineralized bone matrix and a clot producing material comprising polyethylene glycol having an average molecular weight between about 1,500 and about 10,000 MW, wherein the biocompatible material promotes blood clotting in or near a bone defect in a patient, the demineralized bone matrix and PEG being in a ratio of from about 1:9 to about 3:2.

2. The biocompatible material for promoting blood clotting according to claim 1, wherein the demineralized bone matrix is a fibrous demineralized bone matrix.

3. The biocompatible material for promoting blood clotting according to claim 1, further comprising wicking fiber.

4. The biocompatible material according to claim 3, wherein the wicking fiber comprises milled bone.

5. The biocompatible material according to claim 3, wherein the wicking fiber comprises a biocompatible polymer.

6. The biocompatible material for promoting blood clotting according to claim 1, further comprising aluminum sulfate.

7. The biocompatible material for promoting blood clotting according to claim 1, further comprising non-crystalline starch.

8. The biocompatible material for promoting blood clotting according to claim 1, further comprising amphipathic zwitterions.

9. The biocompatible material for promoting blood clotting according to claim 1, further comprising a polyalcohol.

10. The biocompatible material for promoting blood clotting according to claim 1, further comprising a combination of two or more of aluminum sulfate, non-crystalline starch, amphipathic zwitterions, or a polyalcohol.

11. The biocompatible material for promoting blood clotting according to claim 3, wherein the wicking fiber is tube-like.

12. The biocompatible material for promoting blood clotting according to claim 1, further comprising ammonium sulfate.

13. The biocompatible material for promoting blood clotting according to claim 1, further comprising a hydrogel.

14. The biocompatible material for promoting blood clotting according to claim 1, further comprising absorptive, unsintered hydroxyapatite.

15. The biocompatible material for promoting blood clotting according to claim 1, further comprising calcium phosphate.

16. The biocompatible material for promoting blood clotting according to claim 1, further comprising a sieve-like material that draws up water but not clotting factors or platelet molecules.

* * * * *